US009839518B2

(12) United States Patent
Cartledge et al.

(10) Patent No.: US 9,839,518 B2
(45) Date of Patent: Dec. 12, 2017

(54) METHOD OF POST-OPERATIVE ADJUSTMENT FOR MITRAL VALVE IMPLANT

(75) Inventors: Richard G. Cartledge, Hollywood, FL (US); James I. Fann, Portola Valley, CA (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 707 days.

(21) Appl. No.: 13/123,768

(22) PCT Filed: Oct. 20, 2009
(Under 37 CFR 1.47)

(86) PCT No.: PCT/US2009/061285
§ 371 (c)(1),
(2), (4) Date: Apr. 12, 2011

(87) PCT Pub. No.: WO2010/048151
PCT Pub. Date: Apr. 29, 2010

(65) Prior Publication Data
US 2012/0203330 A1    Aug. 9, 2012

Related U.S. Application Data

(60) Provisional application No. 61/106,790, filed on Oct. 20, 2008.

(51) Int. Cl.
*A61F 2/24* (2006.01)

(52) U.S. Cl.
CPC ...... *A61F 2/2448* (2013.01); *A61F 2250/001* (2013.01)

(58) Field of Classification Search
CPC ........ A61F 2/2448; A61F 2/24; A61F 2/2445; A61F 2/2427; A61F 2/243; A61F 2/2436;
(Continued)

(56) References Cited

U.S. PATENT DOCUMENTS 3,537,451 A * 11/1970 Beck et al. ............... 604/165.03
3,575,225 A * 4/1971 Muheim ...................... 383/206
(Continued)

FOREIGN PATENT DOCUMENTS

WO    2008085814 A2    7/2008
WO    2008097999 A2    8/2008

OTHER PUBLICATIONS

Letter dated Jan. 27, 2011 from Richard H. Levinstein, Esq.
(Continued)

*Primary Examiner* — Alexander Orkin
(74) *Attorney, Agent, or Firm* — Lerner, David, Littenberg, Krumholz & Mentlik, LLP

(57) ABSTRACT

The present invention is directed to a mechanism and procedure for adjusting a cardiac implant during the early post-operative period, such as, for example, the first 2-5 days after surgery. During the implant procedure, an adjustment tool is releasably attached to the adjustable implant. The adjustment tool remains connected to the implant following the procedure and extends from the patient's body to allow for post-operative adjustment under normal beating heart conditions. Once the implant is adjusted, the adjustment tool is configured to release from the implant and be removed from the patient's body without requiring access to the patient's heart.

13 Claims, 6 Drawing Sheets

(58) Field of Classification Search

CPC .... A61F 2/2439; A61F 2/2442; A61F 2/2466; A61F 2250/0004; A61F 2250/0006; A61F 2250/0007; A61F 2250/0008; A61F 2250/0009; A61F 2250/001; A61F 2250/0012; A61F 2019/103; A61F 2019/0287; A61F 2002/9517; A61B 2019/0267; A61B 19/02; A61B 2017/0237; A61B 2017/00243; A61B 2017/00369; A61B 2017/00357; A61B 2017/00363; A61B 2017/00375; A61B 2017/0038; A61B 2017/00386; A61B 2017/00392; A61B 2017/00404; A61B 2017/00416; A61B 2017/00422; A61B 2017/00428

USPC ........................................ 623/2.11, 2.36, 2.37

See application file for complete search history.

(56) References Cited

U.S. PATENT DOCUMENTS

| | | | | |
|---|---|---|---|---|
| 3,696,920 | A | * | 10/1972 | Lahay ........................ 206/370 |
| 4,501,363 | A | * | 2/1985 | Isbey, Jr. .................... 206/570 |
| 4,602,911 | A | * | 7/1986 | Ahmadi et al. ............. 623/2.37 |
| 4,646,722 | A | * | 3/1987 | Silverstein et al. .......... 600/104 |
| 5,613,937 | A | | 3/1997 | Garrison et al. |
| 5,938,646 | A | * | 8/1999 | Carter ......................... 604/317 |
| 6,451,054 | B1 | * | 9/2002 | Stevens ....................... 623/2.11 |
| 6,485,495 | B1 | * | 11/2002 | Jenkinson ............... A61B 17/14 606/167 |
| 6,537,114 | B2 | | 3/2003 | Evans |
| 7,175,660 | B2 | | 2/2007 | Cartledge et al. |
| 7,291,156 | B1 | * | 11/2007 | Perone ................. A61B 17/442 606/122 |
| 7,297,150 | B2 | | 11/2007 | Cartledge et al. |
| 7,455,690 | B2 | | 11/2008 | Cartledge et al. |
| 2002/0042651 | A1 | * | 4/2002 | Liddicoat et al. ........... 623/2.11 |
| 2003/0050693 | A1 | * | 3/2003 | Quijano et al. ............. 623/2.11 |
| 2003/0158505 | A1 | * | 8/2003 | Calvert ........................ 601/110 |
| 2003/0199975 | A1 | * | 10/2003 | Gabbay ....................... 623/2.36 |
| 2004/0148021 | A1 | * | 7/2004 | Cartledge et al. ........... 623/2.37 |
| 2005/0173274 | A1 | * | 8/2005 | Gammons ................... 206/320 |
| 2006/0015178 | A1 | | 1/2006 | Moaddeb et al. |
| 2006/0106405 | A1 | | 5/2006 | Fann et al. |
| 2006/0241748 | A1 | | 10/2006 | Lee et al. |
| 2007/0000498 | A1 | * | 1/2007 | Glynn et al. ................ 128/852 |
| 2007/0016287 | A1 | | 1/2007 | Cartledge et al. |
| 2007/0051377 | A1 | | 3/2007 | Douk et al. |
| 2007/0142907 | A1 | * | 6/2007 | Moaddeb et al. ........... 623/2.11 |
| 2007/0276478 | A1 | * | 11/2007 | Marmureanu et al. ...... 623/2.11 |
| 2007/0299543 | A1 | | 12/2007 | Cartledge et al. |
| 2008/0027483 | A1 | | 1/2008 | Cartledge et al. |
| 2008/0109076 | A1 | | 5/2008 | Cartledge et al. |
| 2008/0306586 | A1 | | 12/2008 | Cartledge et al. |
| 2009/0125102 | A1 | | 5/2009 | Cartledge et al. |
| 2009/0234404 | A1 | | 9/2009 | Fitzgerald et al. |
| 2009/0248148 | A1 | * | 10/2009 | Shaolian et al. ............ 623/2.37 |
| 2010/0305609 | A1 | | 12/2010 | Cartledge et al. |
| 2011/0009956 | A1 | | 1/2011 | Cartledge et al. |
| 2011/0022168 | A1 | | 1/2011 | Cartledge |
| 2011/0066231 | A1 | | 3/2011 | Cartledge et al. |
| 2011/0093062 | A1 | | 4/2011 | Cartledge et al. |
| 2011/0196480 | A1 | | 8/2011 | Cartledge |
| 2011/0202130 | A1 | | 8/2011 | Cartledge et al. |
| 2011/0208295 | A1 | | 8/2011 | Cartledge et al. |
| 2011/0257633 | A1 | | 10/2011 | Cartledge et al. |

OTHER PUBLICATIONS

International Search Report for Application No. PCT/US09/61285 dated Feb. 3, 2010.

U.S. Appl. No. 60/801,861, filed May 19, 2006.

U.S. Appl. No. 60/878,068, filed Jan. 3, 2007.

U.S. Appl. No. 61/084,446, filed Jul. 29, 2008.

\* cited by examiner

METHOD OF POST-OPERATIVE ADJUSTMENT FOR MITRAL VALVE IMPLANT

CROSS-REFERENCE TO RELATED APPLICATIONS

The present application is a national phase entry under 35 U.S.C. §371 of International Application No. PCT/US2009/61285, filed Oct. 20, 2009, which claims priority from U.S. Provisional Application No. 61/106,790, filed Oct. 20, 2008, all of which are hereby incorporated herein by reference.

FIELD OF THE INVENTION

This invention relates generally to implantable devices and methods for controlling the shape and/or size of an anatomical structure or lumen, including minimally invasive adjustment techniques.

BACKGROUND

Many anatomic structures in the mammalian body are hollow passages in which walls of tissue define a central lumen, which serves as a conduit for blood, other physiologic fluids, nutrient matter, or waste matter passing within the structure. In many physiologic settings, dysfunction may result from a structural lumen which is either too large or too small. In most such cases, dysfunction can be relieved by interventional changes in the luminal size.

Thus in surgery, there is often a need to adjust the internal circumference of an orifice or other open anatomic structure to modify the size of the orifice or opening to achieve a desired physiologic effect. Often, such surgical procedures require interruption in the normal physiologic flow of blood, other physiologic fluids, or other structural contents through the orifice or structure. The exact amount of the modulation required for the desired effect often cannot be fully appreciated until physiologic flow through the orifice or structure is resumed. It would be advantageous, therefore, to have an adjustable means of achieving this modulating effect, such that the degree of modification could be changed after implantation of a device, including after the resumption of normal flow in situ.

One example of a dysfunction within an anatomic lumen is in the area of cardiac surgery, and specifically valvular repair. Approximately seven hundred thousand open heart surgical procedures are now performed annually in the United States, and as many as twenty percent of these operations are related to cardiac valves. For example, mitral valve repair has become one of the most rapidly growing areas in adult cardiac surgery today.

Two essential features of mitral valve repair are to fix primary valvular pathology (if present) and to support the annulus or reduce the annular dimension using a prosthesis that is commonly in the form of a ring or band. The problem encountered in mitral valve repair is the surgeon's inability to fully assess the effectiveness of the repair until the heart has been fully closed, and the patient is weaned off cardiopulmonary bypass. Once this has been achieved, valvular function can be assessed in the operating room using, for example, transesophageal echocardiography (TEE). If significant residual valvular insufficiency is then documented, the surgeon must, in conventional procedures, re-arrest the heart, re-open the heart, and then re-repair or replace the valve. This increases overall operative, anesthesia, and bypass times, and therefore increases the overall operative risks.

If the prosthesis used to reduce the annulus is larger than the ideal size, for example, mitral insufficiency may persist. If the prosthesis is too small, for example, mitral stenosis may result. The need exists, therefore, for an adjustable prosthesis that would allow a surgeon to adjust the annular dimension in situ in a beating heart under TEE guidance or other diagnostic modalities to achieve optimal valvular sufficiency and function.

There remains a need in the art for methods and apparatus that will facilitate post-operative adjustment of a prosthetic implant to reduce the diameter of such a mitral annulus in a percutaneous or other minimally invasive procedure, while still achieving clinical and physiologic results that are at least the equivalent of the yields of the best open surgical procedures for these same problems.

SUMMARY

Accordingly, the invention is directed to a mechanism and procedure for adjusting a cardiac implant, such as an adjustable mitral valve ring, after implant in the early postoperative period, such as in the first 2-5 days after surgery. The cardiac implant device can be delivered to the site of implantation through an open heart surgical procedure, a minimally invasive procedure, percutaneously or robotically. During the implant procedure, an adjustment tool is releasably attached to the adjustable surgical implant. The adjustment tool remains connected to the implant following the procedure and extends from the patient's body to allow for post-operative adjustment under normal beating heart conditions. Once the implant is adjusted, the tool is configured to release from the implant and be removed without further access to the heart.

In one embodiment, the invention provides a method for adjusting the internal dimensions of an annulus of a patient's heart. The method includes the step of exposing the mitral valve. Next, the method includes securing an adjustable implant ring to the tissue adjacent the annulus. In one embodiment, another step includes creating a right atriotomy and advancing the adjustment tool through the heart's atrial septum into the left atrium. The method further includes releasably attaching the adjustment tool to the adjustable implant ring so as to allow for adjustment of the ring dimensions using the tool. Other steps include closing the atriotomies and resuming blood flow through the heart. Finally, the method includes adjusting the adjustable implant ring using the adjustment tool in the post-operative period as it extends outside the patient via the internal jugular vein, subclavian vein or femoral vein. It is understood that in alternative methods, an atriotomy may be created in the left atrium to the exterior of the heart for either the insertion of the adjustable implant and/or exiting of the post-surgical adjustment tool.

The above described methods are just examples of the present invention. The methods may vary in other embodiments, including different anatomical points of access and egress. In one embodiment, after implantation of the ring, the adjustment tool may exit the heart through the pulmonary vein. In another embodiment, after implantation of the ring, the adjustment tool may exit the heart directly through an atriotomy incision. The adjustment tool extends from the atriotomy incision through the chest wall via an intercostal space.

In certain embodiments, at least one suture and a plurality of pledgets, or an auto-purse string tensioning device, are inserted around the atriotomy incision prior to or after the adjustment tool exists through the incision, and the sutures are pulled tight to maintain hemostasis around the adjustment tool during its implantation and again following its removal through the atriotomy incision.

In another embodiment, the adjustment tool may enter and/or exit the heart through the pulmonary vein.

BRIEF DESCRIPTION OF FIGURES

The accompanying drawings, which are included to provide further understanding of the invention and are incorporated in and constitute a part of this specification, illustrate embodiments of the invention and together with the description serve to explain the principles of the invention. In the drawings.

DETAILED DESCRIPTION OF THE INVENTION

Reference will now be made in detail to the preferred embodiments of the present invention, examples of which are illustrated in the accompanying drawings. However, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The present invention provides a mechanism and procedure for adjusting an adjustable surgical implant, such as a mitral valve ring, after an open surgical implant procedure. During the open surgical implant procedure, an adjustment tool is releasably attached to the adjustable surgical implant. After the implant is secured and the surgeon's open heart incision is closed and the patient's heart re-started, the adjustment tool remains connected to the implant and the tool extends from the patient's body to allow for adjustment of the implant at a later time. Preferably, adjustments are made about 2-5 days after the initial surgical procedure to allow for the heart to fully stabilize and the for the effects of anesthesia to fully dissipate. Once the implant is adjusted, the tool can be released from the implant and removed without further access to the heart.

Implantable devices for controlling the internal circumference of an anatomic orifice or lumen have been disclosed in previous applications, including U.S. Pat. No. 7,297,150 filed Aug. 29, 2003, PCT/US08/00014 filed Jan. 3, 2008, PCT/US08/53084 filed Feb. 5, 2008, and U.S. Provisional Application No. 60/61,084,446 filed Jul. 29, 2008, which are incorporated herein by reference in their entirety.

Figure 1A:
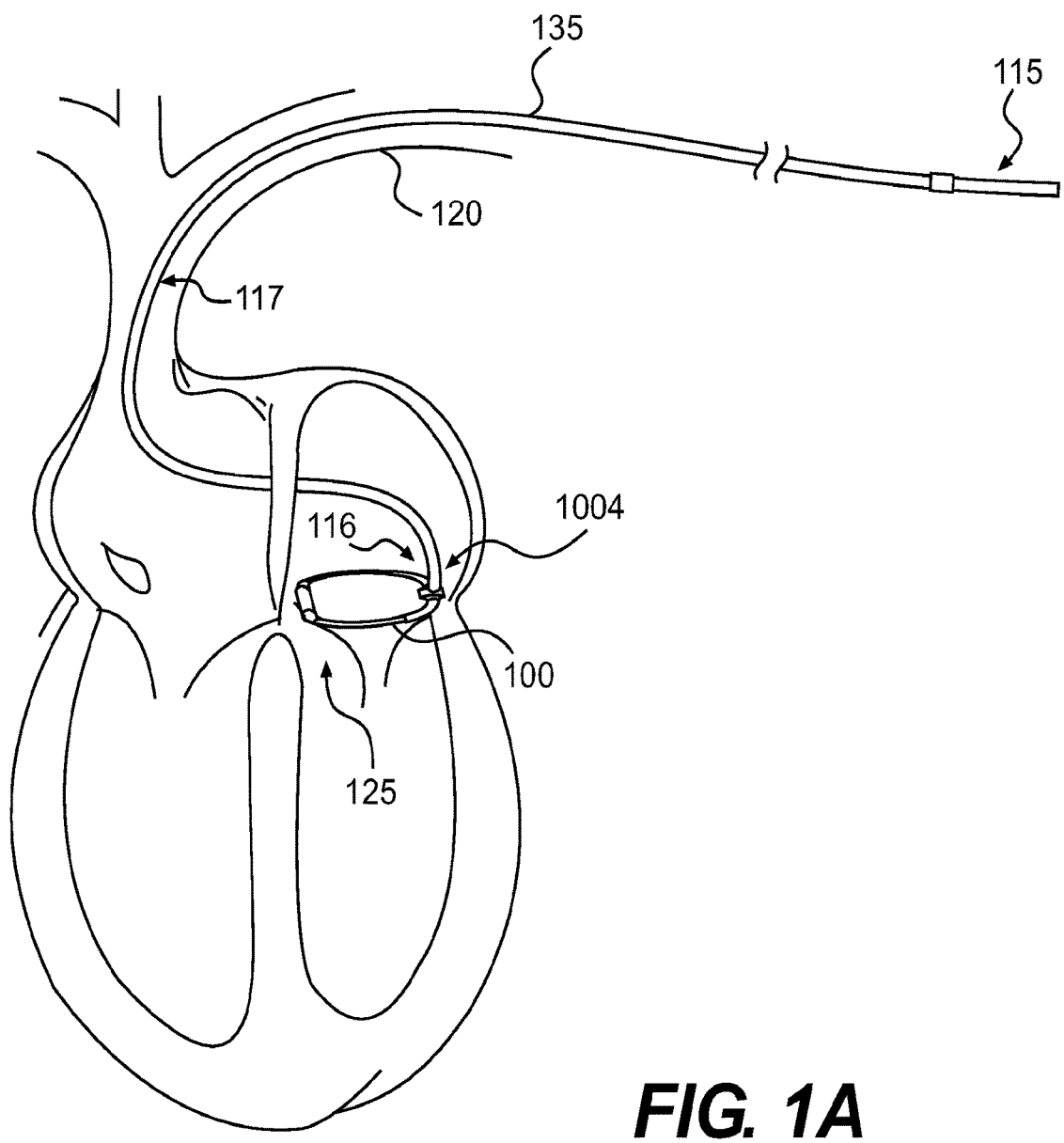
FIG. 1A provides a schematic of the adjustment tool path in accordance with one embodiment of the invention.
Figure 1B:
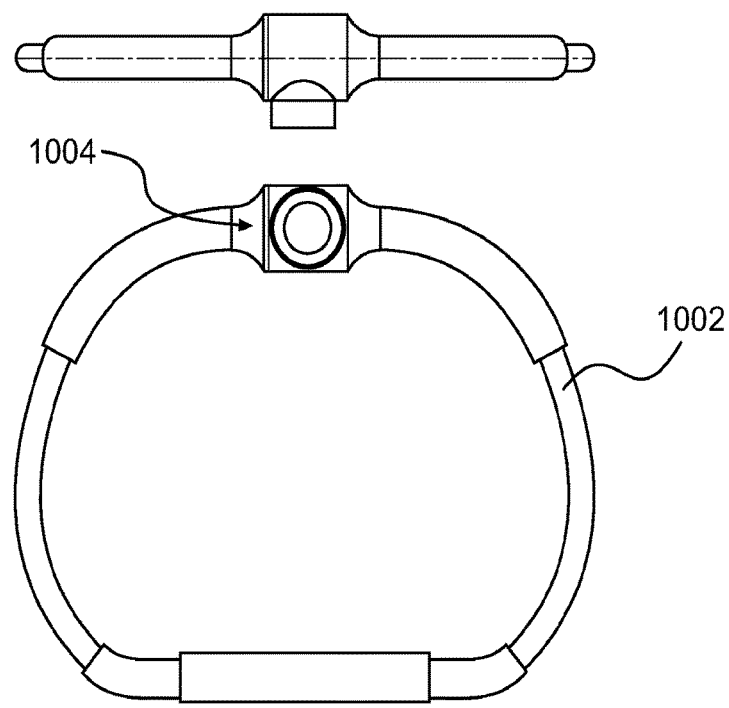
FIG. 1B provides a schematic view of an adjustable implant for use in accordance with embodiments of the present invention.

FIG. 1A provides a schematic view of the adjustment tool path in accordance with an embodiment of the invention. The implant (annuloplasty ring) 100 is sutured to the annulus of a patient's mitral valve 125. To adjust the implant 100, an adjustment tool 135 is inserted though an accessible passage and operatively connected to an adjustable member on the implant 100. An example of the implant 100 with the adjustable member 1004 is shown in FIG. 1B. The adjustable member may include a gear, set of gears or other mechanism to allow for a change in one or more dimensions of the implant 100.

Figure 1C:
FIG. 1C provides a schematic view of an adjustment tool for use in accordance with embodiments of the present invention.

Referring again to FIG. IA, the adjustment tool 135 includes a handle portion 115, and a distal tip portion 116. The distal tip portion operably engages with the implant 100 generally, and with the adjustable member 1004, in particular, to impart movement and dimensional change to the implant 100. Between the handle portion 115 and the distal tip 116 of the adjustment tool 135 is a flexible shaft 117. Movement of the handle portion 115 causes motion to be transferred through the shaft 117 to allow the distal tip portion 116 to effectively adjust the implant 100 when the distal tip portion 116 is operable engaged with the adjustable member 1004 of the implant 100. The shaft 117 of the adjustment tool 135 may include two or more portions, such as a sheath covering an inner flexible cable. The shaft 117 will be flexible yet strong, and can be bent or curved during use without breaking and without destroying its ability to guide and rotate the inner cable, so as to operably control an the adjustable member 1004 of the adjustable implant 100. FIG. 1C provides an example of an adjustment tool suitable for use with methods of the present invention. Other embodiments of the adjustment tool 135 are disclosed in Applicant's co-pending and commonly assigned U.S. Provisional Application Nos. 60/878,068 and 60/801,861, previously incorporated herein by reference. The adjustment tool 135 is then manipulated, e.g., rotated, depending upon the design of the adjustable member 1004 in the implant 100, to cause the adjustable member 1004 to change the size and/or shape of the implant 100, and hence the underlying mitral annulus 125 to which it is sutured. Upon completion of the implant procedure, the adjustment tool 135 is left extending through the introductory incision for post-operative adjustment. The adjustment tool 135 may pass through the atrial septum and exit the left subclavian vein 120 (as shown in FIG. 1A) or may exit the internal jugular vein or right subclavian vein.

Figure 2:
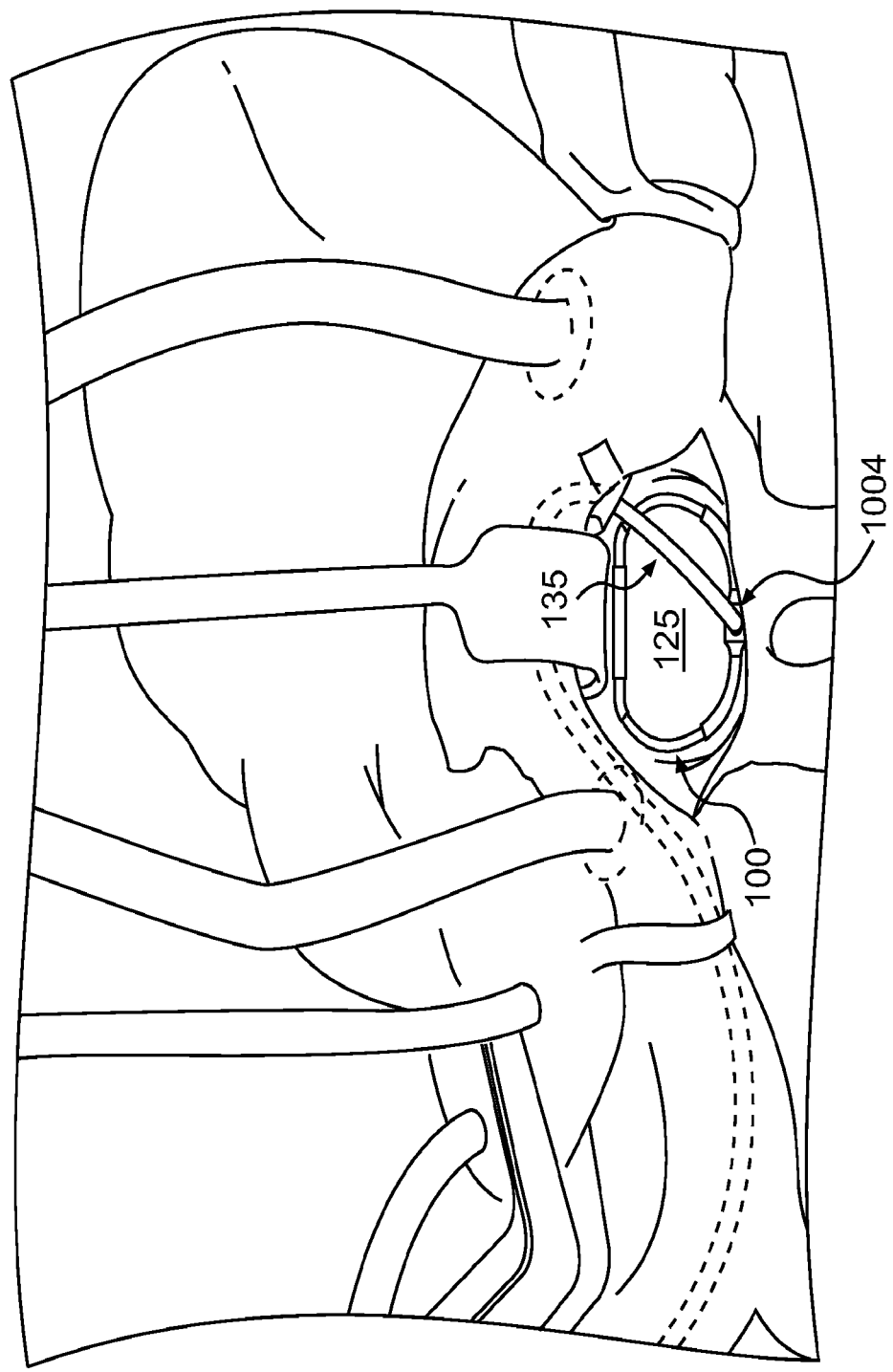
FIG. 2 provides a left atriotomy view of an implant and adjustment tool in accordance with one embodiment of the invention.

FIG. 2 provides a left atriotomy view of the ring implant 100 and adjustment tool 135 in accordance with an embodiment of the invention. As shown in FIG. 2, the adjustable implant 100 is affixed to the annulus of a mitral valve 125. As shown in FIG. 1B, the exemplary adjustable implant 100 is further provided with adjustable member 1004 that is controlled by the attached or coupled adjustment tool 135. The tool 135 passes through the atrial septum and into the right atrium and subclavian vein. After closure of the myocardial incision, the adjustment tool 135 remains attached or coupled to the implant 100, so that the size and shape of the implant 100 may further be affected after physiologic flow through the heart is resumed. Adjustments may be made both while the chest incision is still open and after the chest incision has been closed. Once the desired shape and function of the implant are achieved, the adjustment tool 135 may be disengaged from the implant 100 and withdrawn. Should further adjustments to the implant 100 be needed after the adjustment tool 135 has been disengaged, the adjustment tool can be re-attached and further adjustments made in a separate surgical procedure.

Figure 3:
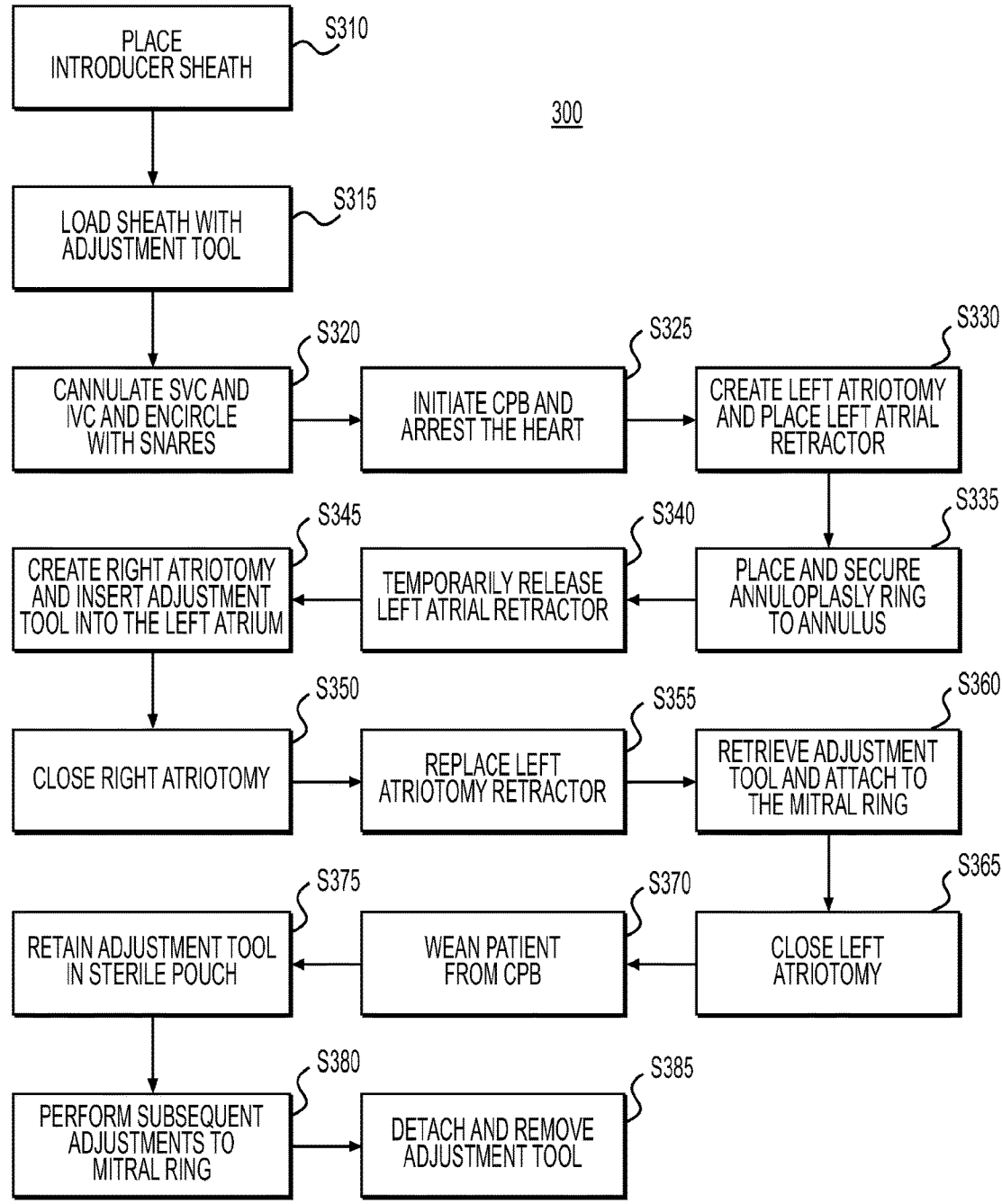
FIG. 3 provides a flow chart for a procedure for implanting and adjusting a mitral valve ring in accordance with one embodiment of the present invention.

Referring to FIG. 3, a flow chart for a procedure 300 for implanting and adjusting a mitral valve ring is provided. In step S310, during the implant procedure where the implant will be secured to the tissue adjacent the mitral valve annulus, the anesthesiologist or surgeon would place an additional introducer sheath into either the internal jugular or subclavian vein right after induction of anesthesia (one may be conventionally placed for central vein access and/or a Swan-Ganz catheter). The introducer sheath for the adjustment tool may be the same type of sheath currently used to introduce the Swan-Ganz catheter. The introducer sheath is inserted into the subclavian or internal jugular vein using the Seldinger technique with a guidewire and obturator. The guidewire and obturator are removed followed by the placement of the adjustment tool. The length of the sheath is approximately 10-15 cm in length.

In step S315, the introducer sheath is loaded with a sterile flexible adjustment tool placed in a sterile sleeve, such as, for example, the adjustment tool 135 discussed above with respect to FIGS. 1 and 2.

In the next step S320, at the time of cardiac cannulation, the superior vena cava (SVC) and inferior vena cava (IVC) are cannulated and encircled with snares to provide access to the right atrium as necessary after initiating cardiopulmonary bypass.

In step S325, cardiopulmonary bypass is initiated and the aortic is cross-clamped The heart is arrested using cardioplegic solution, after which, in step S330, a left atriotomy is created and a left atrial retractor placed to visualize and access the mitral valve.

In step S335, an adjustable mitral annuloplasty ring is placed and secured to the annulus. Placing and securing the annuloplasty ring may be accomplished using a variety of conventional means. Placement and attachment means are further disclosed in the above mentioned, prior-filed applications, each of which are incorporated herein by reference in their entirety.

Next, in step S340, the left atrial retractor is temporarily released. A small right atriotomy is made in step S345 and the adjustment tool advanced and directed through the atrial septum into the left atrium, preferably under direct vision of the surgeon. Then, in step S350, the right atriotomy is closed.

In step S355, the left atriotomy retractor is replaced again, exposing the left atrium. Then, in step S360, the adjustment tool is retrieved and releasably attached to the mitral ring to allow for adjustment of the ring dimensions using the tool. After the adjustment tool is attached to the ring, in step S365, the left atriotomy is closed in conventional fashion.

In step S370, the patient is weaned from the cardiopulmonary bypass (CPB). Any further adjustments to the mitral valve implant may be made at this point in the operating room using the adjustment tool. After this initial period of adjustments, in step S375, the adjustment tool is retained in a sterile pouch for use in later adjustments. The sterile pouch may be, for example, a conventional sterile pouch typically used in a cardiac catheterization laboratory ("cath lab") or a sterile pouch used to protect a Swan-Ganz catheter. The patient may then be transferred to another location outside the operating area, such as a cath lab, to await recovery and resumption of normal blood flow conditions. As an example, a 2-5 day window may be preferable to ensure a return to normal conditions before adjustments are made. However, adjustments may be made at virtually any interval after surgery.

In step S380, such additional adjustments to the mitral valve implant may be made using the adjustment tool. These adjustments allow adjustment of the annular dimension in situ in a beating heart under, for example, transesophageal echocardiography (TEE) guidance or other diagnostic modalities to achieve optimal valvular sufficiency and function. It is contemplated that multiple adjustments may be made, if necessary, using the adjustment tool over various time intervals.

In step 385, after any adjustments are complete (and preferably verified via TEE, TTE (transthoracic echocardiography) or other diagnostic means), the adjustment tool is detached and removed from the jugular or subclavian sheath. The sheath is then also removed and a sterile dressing placed over the wound as is done conventionally. The defect in the atrial septum is sufficiently small to close under natural body conditions.

The above described method is only one example of how to perform post-operative adjustment using the present invention. In other embodiments, the anatomical point of access for the adjustment tool may vary. The steps of the surgical procedure would otherwise be similar and would be understood by one of skill in the art.

Figure 4:
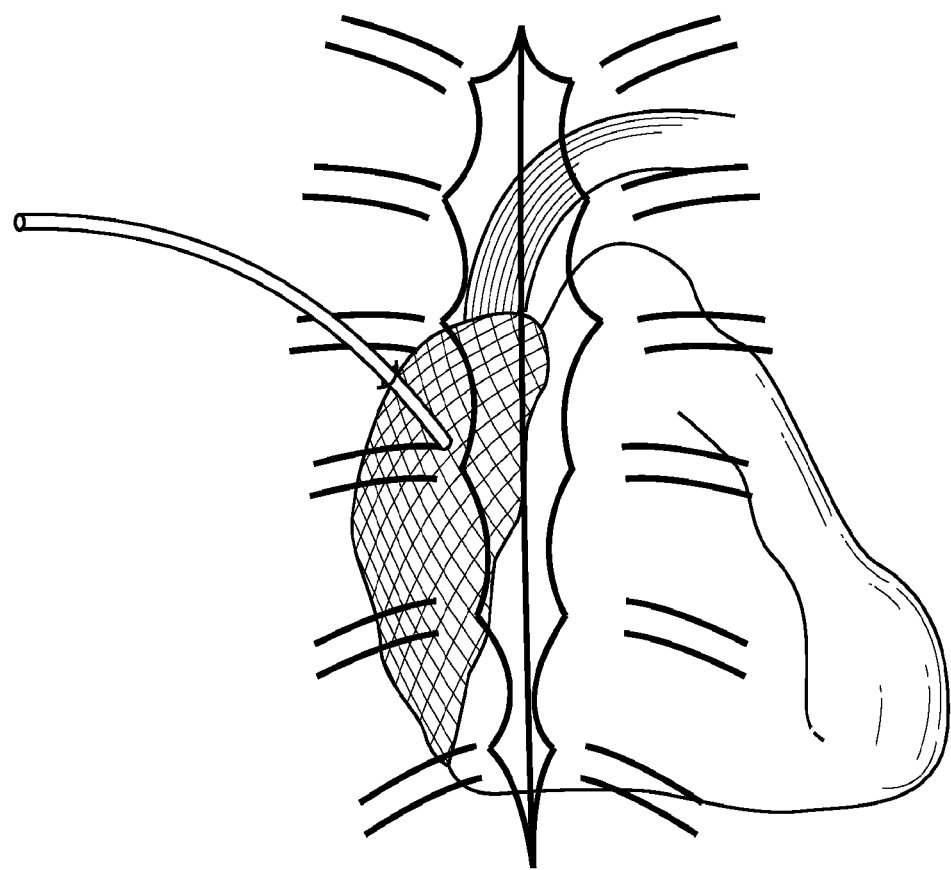
FIG. 4 provides a schematic view of the heart with an adjustment tool extending through an atriotomy incision, as in one embodiment of the invention.
Figure 5A:
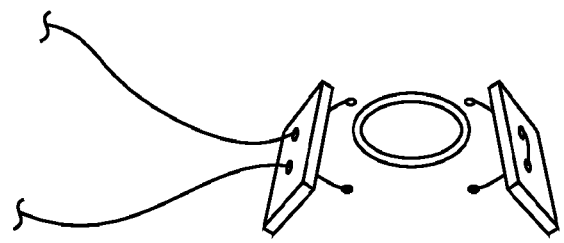
FIG. 5 provides a series of schematic views of a method according to one embodiment of the invention.
Figure 5B:
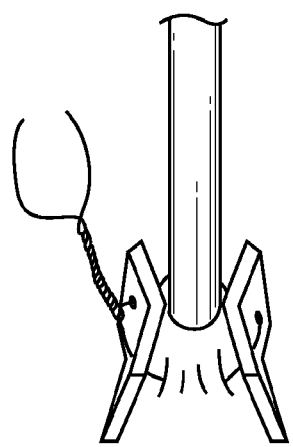
Figure 5C:
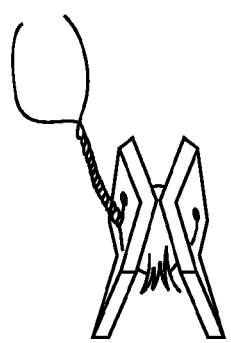

In one embodiment, the adjustment tool enters and exits the heart directly through the atriotomy incision. In such an embodiment, at least one suture, and preferably two sutures, are inserted into the tissue surrounding the atriotomy incision prior to insertion of the adjustment tool. Using these sutures, two prolene pledgets are secured onto the surface of the tissue on opposite sides of the atriotomy incision. The adjustment tool is inserted through the sutures and pledgets, and the sutures are pulled taut using a knot-pusher to pull the pledgets together, whereby hemostasis is maintained around the adjustment tool. Upon removal of the adjustment tool from the atriotomy incision, the sutures are again pulled taut to create hemostasis using the pledgets. FIG. 4 shows an adjustment tool extending through an atriotomy incision, as in this embodiment. FIG. 5 shows various points of operation of this embodiment. In the first view, a suture and pledgets have been placed around an atriotomy incision. In the second view, an adjustment tool has been inserted through the atriotomy incision, and the sutures and pledgets are pulled tight around the tool. In the third view, the suture and pledgets have been pulled tight to create hemostatis following removal of the adjustment tool from the atriotomy incision.

In a further embodiment, the adjustment tool accesses the implant via a vein, preferably a pulmonary vein. After desired adjustments have been made, the adjustment tool can be removed through a pulmonary vein, rather than an incision in the heart tissue. Such removal may advantageously be less traumatic than removal through an incision.

While exemplary embodiments of the invention have been shown and described herein, it will be obvious to those skilled in the art that such embodiments are provided by way of example only. Numerous insubstantial variations, changes, and substitutions will now be apparent to those skilled in the art without departing from the scope of the invention disclosed herein by the Applicants. Accordingly, it is intended that the invention be limited only by the spirit and scope of the claims, as they will be allowed.

The invention claimed is:

1. A method of performing on a patient a post-operative adjustment of the internal dimensions of an annulus of a patient's heart, said method comprising the steps of:
arresting the heart and creating a left atriotomy;
securing an adjustable implant ring to the tissue adjacent the annulus, the adjustable implant ring having an adjustable member operative for changing the dimension and/or shape of the adjustable implant ring;
creating a right atriotomy;
advancing an adjustment tool through the heart's atrial septum into the left atrium, wherein the adjustment tool includes a flexible shaft having a flexible sheath covering an elongated inner flexible cable;
releasably attaching the adjustment tool to the adjustable implant ring by releasably attaching the inner flexible cable to the adjustable member so as to allow for adjustment of the implant ring dimensions using the tool by rotation of the inner flexible cable causing rotation of the adjustable member, the tool having a portion extending outside the patient's body;
closing the left atriotomy;
resuming blood flow through the heart;
first adjusting the adjustable implant ring after resuming blood flow using the adjustment tool while attached to the adjustable implant ring from outside the patient's body, the adjustment tool having a proximal portion remaining outside the patient's body;
placing the proximal portion of the adjustment tool in a sterile pouch after the first adjusting step;
leaving the adjustment tool attached to the adjustable implant ring within the patient's body during a post-operative period;
retaining the proximal portion of the adjustment tool after the first adjusting step in the sterile pouch during the post-operative period for use in later adjustments of the adjustable implant ring; and
second adjusting the adjustable implant ring during the post-operative period from outside the patient's body using the adjustment tool while attached to the adjustable implant ring.

2. The method of claim 1, further comprising the steps of:
detaching the adjustment tool from the adjustable implant ring; and
removing the adjustment tool from the patient's body after adjusting the adjustable implant during the post-operative period.

3. The method of claim 2, further comprising the steps of:
reinserting the adjustment tool into the patient's body;
reattaching the adjustment tool to the adjustable implant ring so as to allow for adjustment of the ring dimensions using the tool; and
adjusting the adjustable implant ring using the adjustment tool from outside the patient's body.

4. A method of performing on a patient a post-operative adjustment of the internal dimensions of an annulus of a patient's heart; said method comprising the steps of:
arresting the heart and creating an atriotomy;
securing an adjustable implant ring to the tissue adjacent the annulus, the adjustable implant ring having an adjustable member operative for changing the dimension and/or shape of the adjustable implant ring;
creating an incision in the pulmonary vein;
advancing an adjustment tool into the left atrium, wherein the adjustment tool includes a flexible shaft having a flexible sheath covering an elongated inner flexible cable;
releasably attaching the adjustment tool to the adjustable implant ring by releasably attaching the inner flexible cable to the adjustable member so as to allow for adjustment of the implant ring dimensions using the tool by rotation of the inner flexible cable causing rotation of the adjustable member, the tool having a portion extending outside the patient's body;
closing the atriotomy;
resuming blood flow through the heart;
first adjusting the adjustable implant ring after resuming blood flow using the adjustment tool while attached to the adjustable implant ring from outside the patient's body, the adjustment tool having a proximal portion remaining outside the patient's body;
placing the proximal portion of the adjustment tool in a sterile pouch after the first adjusting step;
leaving the adjustment tool attached to the adjustable implant ring within the patient's body during a post-operative period;
retaining the proximal portion of the adjustment tool after the first adjusting step in the sterile pouch during the post-operative period for use in later adjustments of the adjustable implant ring; and.
second adjusting the adjustable implant ring during the post-operative period from outside the patient's body using the adjustment tool while attached to the adjustable implant ring.

5. The method of claim 4, further comprising the steps of;
detaching the adjustment tool from the adjustable implant ring; and
removing the adjustment tool from the patient's body after adjusting the adjustable implant during the post-operative period.

6. The method of claim 5, further comprising the steps of:
reinserting the adjustment tool into the patient's body;
reattaching the adjustment tool to the adjustable implant ring so as to allow for adjustment of the ring dimensions using the tool; and
adjusting the adjustable implant ring using the adjustment tool from outside the patient's body.

7. A method of performing on a patient a post-operative adjustment of the internal dimensions of an annulus of a patient's heart, said method comprising the steps of:
arresting the heart and creating an atriotomy;
securing an adjustable implant ring to the tissue adjacent the annulus, the adjustable implant ring having an adjustable member operative for changing the dimension and/or shape of the adjustable implant ring;
creating an incision in the left atrium;
advancing an adjustment tool through the incision, wherein the adjustment tool includes a flexible shaft having a flexible sheath covering an elongated inner flexible cable;
releasably attaching the adjustment tool to the adjustable implant ring by releasably attaching the inner flexible cable to the adjustable member so as to allow for adjustment of the implant ring dimensions using the tool by rotation of the inner flexible cable causing rotation of the adjustable member, the tool having a portion extending outside the patient's body;
closing the atriotomy;
resuming blood flow through the heart; and
first adjusting the adjustable implant ring after resuming blood flow using the adjustment tool while attached to the adjustable implant ring from outside the patient's body, the adjustment tool having a proximal portion remaining outside the patient's body;

placing the proximal portion of the adjustment tool in a sterile pouch after the first adjusting step;

leaving the adjustment tool attached to the adjustable implant ring within the patient's body during a post-operative period;

retaining the proximal portion of the adjustment tool after the first adjusting step in the sterile pouch during the post-operative period for use in later adjustments of the adjustable implant ring; and second adjusting the adjustable implant ring during the post-operative period from outside the patient's body using the adjustment tool while attached to the adjustable implant ring.

8. The method of claim 7, further comprising the steps of:

detaching the adjustment tool from the adjustable implant ring; and removing the adjustment tool from the patient's body after adjusting the adjustable implant during the post-operative period.

9. The method of claim 8, further comprising the steps of:

reinserting the adjustment tool into the patient's body;

reattaching the adjustment tool to the adjustable implant ring so as to allow for adjustment of the ring dimensions using the tool; and adjusting the adjustable implant ring using the adjustment tool from outside the patient's body.

10. The method of claim 7, further comprising the steps of:

inserting at least one suture and a plurality of pledgets around an incision in the left atrium; and pulling the at least one suture tight to maintain hemostasis around the adjustment tool.

11. A method of performing on a patient a post-operative adjustment of the internal dimensions of an annulus of a patient's heart, said method comprising the steps of:

arresting the heart and creating a left atriotomy;

securing an adjustable implant ring having an adjustable member to the tissue adjacent the annulus, the adjustable member operative for changing the dimension and/or shape of the adjustable implant ring;

creating a right atriotomy;

advancing a distal portion of an adjustment tool through the heart's atrial septum into the left atrium, wherein the adjustment tool includes a flexible shaft having a flexible sheath covering an elongated inner flexible cable;

leaving a proximal portion of the adjustment tool extending outside the patient's body through the left atrium;

releasably attaching the distal portion of the adjustment tool mechanically to the adjustable member of the adjustable implant ring by releasably attaching the inner flexible cable to the adjustable member so as to allow for adjustment of the implant ring dimensions using the tool by rotation of the inner flexible cable causing rotation of the adjustable member, the tool having the proximal portion remaining extending outside the patient's body;

resuming blood flow through the heart;

first adjusting the adjustable implant ring after resuming blood flow using the proximal portion of the adjustment tool while the distal portion of the adjustment tool remains mechanically attached to the adjustable member of the adjustable implant ring from outside the patient's body;

placing the proximal portion of the adjustment tool in a sterile pouch to provide a sterile environment after the first adjusting step;

leaving the adjustment tool mechanically attached to the adjustable member of the adjustable implant ring within the patient's body during a post-operative period and the proximal portion of the adjustment tool outside of the patient's body;

second adjusting the adjustable implant ring during the post-operative period from outside the patient's body using the adjustment tool while extending through the left atrium and while mechanically attached to the adjustable member of the adjustable implant ring; and maintaining the proximal portion of the adjustment tool after the first adjusting step in the sterile environment during the post-operative period.

12. A method of performing on a patient a post-operative adjustment of the internal dimensions of an annulus of a patient's heart; said method comprising the steps of:

arresting the heart and creating an atriotomy;

securing an adjustable implant ring having an adjustable member to the tissue adjacent the annulus, the adjustable member operative for changing the dimension and/or shape of the adjustable implant ring;

creating an incision in the pulmonary vein;

advancing a distal portion of an adjustment tool into the left atrium, wherein the adjustment tool includes a flexible shaft having a flexible sheath covering an elongated inner flexible cable;

releasably attaching the distal portion of the adjustment tool to the adjustable member of the adjustable implant ring by releasably attaching the inner flexible cable to the adjustable member so as to allow for adjustment of the implant ring dimensions using the tool by rotation of the inner flexible cable causing rotation of the adjustable member, the tool having a proximal portion extending outside the patient's body through the left atrium;

resuming blood flow through the heart;

first adjusting the adjustable implant ring after resuming blood flow using the proximal portion of the adjustment tool while attached to the adjustable implant ring from outside the patient's body;

placing the proximal portion of the adjustment tool in a sterile pouch to provide a sterile environment after the first adjusting step;

leaving the adjustment tool mechanically attached to the adjustable member of the adjustable implant ring within the patient's body during a post-operative period and the proximal portion of the adjustment tool outside of the patient's body;

second adjusting the adjustable implant ring during the post-operative period from outside the patient's body using the adjustment tool while extending through the left atrium and while mechanically attached to the adjustable member of the adjustable implant ring; and maintaining the proximal portion of the adjustment tool after the first adjusting step in the sterile environment during the post-operative period.

13. A method of performing on a patient a post-operative adjustment of the internal dimensions of an annulus of a patient's heart, said method comprising the steps of:

arresting the heart and creating an atriotomy;

securing an adjustable implant ring having an adjustable member to the tissue adjacent the annulus, the adjustable member operative for changing the dimension and/or shape of the adjustable implant;

creating an incision in the left atrium;

advancing an adjustment tool having a distal portion through the incision, wherein the adjustment tool includes a flexible shaft having a flexible sheath covering an elongated inner flexible cable;

releasably attaching the distal portion of the adjustment tool mechanically to the adjustable member of the adjustable implant ring by releasably attaching the inner flexible cable to the adjustable member so as to allow for adjustment of the implant ring dimensions using the tool by rotation of the inner flexible cable causing rotation of the adjustable member, the tool having a proximal portion extending outside the patient's body through the left atrium;

resuming blood flow through the heart;

first adjusting the adjustable implant ring after resuming blood flow using the proximal portion of the adjustment tool while the distal portion is mechanically attached to the adjustable member of the adjustable implant ring from outside the patient's body;

placing the proximal portion of the adjustment tool in a sterile pouch to provide a sterile environment after the first adjusting step;

leaving the adjustment tool mechanically attached to the adjustable member of the adjustable implant ring within the patient's body during a post-operative period and the proximal portion of the adjustment tool outside of the patient's body;

second adjusting the adjustable implant ring during the post-operative period from outside the patient's body using the adjustment tool while extending through the left atrium and mechanically attached to the adjustable member of the adjustable implant ring; and maintaining the proximal portion of the adjustment tool after the first adjusting step in the sterile environment during the post-operative period.

\* \* \* \* \*